United States Patent [19]

Matkovich et al.

[11] Patent Number: 4,797,259
[45] Date of Patent: Jan. 10, 1989

[54] WELL-TYPE DIAGNOSTIC PLATE DEVICE

[75] Inventors: Vlado I. Matkovich, Glen Cove; Jerold Martin, New York; Peter J. Degen, Huntington, all of N.Y.

[73] Assignee: Pall Corporation, Glen Cove, N.Y.

[21] Appl. No.: 941,386

[22] Filed: Dec. 15, 1986

[51] Int. Cl.$^4$ ............................................. C12M 1/20
[52] U.S. Cl. ................................. 422/101; 422/102; 435/7; 435/301; 356/246
[58] Field of Search ............... 422/101, 102; 435/7, 435/301; 356/246

[56] References Cited

U.S. PATENT DOCUMENTS

| | | | |
|---|---|---|---|
| 4,066,512 | 1/1978 | Lai et al. | 195/127 |
| 4,090,850 | 5/1978 | Chen et al. | 422/102 X |
| 4,246,339 | 1/1981 | Cole et al. | 435/7 |
| 4,317,726 | 3/1982 | Shepel | 422/101 X |
| 4,407,943 | 10/1983 | Cole et al. | 435/7 |
| 4,493,815 | 1/1985 | Fernwood et al. | 422/101 |

FOREIGN PATENT DOCUMENTS 0098534  1/1984  European Pat. Off. ............ 422/101
86/07606 12/1986  World Int. Prop. O.

Primary Examiner—Barry S. Richman
Assistant Examiner—Jill Johnston
Attorney, Agent, or Firm—Leydig, Voit & Mayer

[57] ABSTRACT

A diagnostic test device is provided including a plate having at least one well, preferably a plurality of wells, each with an open bottom across which a composite membrane comprising three layers is placed, with a hydrophobic, liquid-tight seal provided at the periphery of each well. The composite membrane from the top of upstream side to the bottom or downstream side, in sequence, includes a first reaction or filtration layer formed from a thin, liquophilic, microporous membrane, a second or sealing layer, preferably a hydrophobic material in sheet or fiber form, such as nonwoven polypropylene fibers, and a liquophobic, preferably hydrophobic, barrier layer having one or more apertures which allows liquid to exit the well while eliminating lateral migration of a pendant liquid drop. The liquophobic seal provided by the liquophobic sealing layer eliminates "cross-talk" by lateral diffusion or wicking.

35 Claims, 2 Drawing Sheets

WELL-TYPE DIAGNOSTIC PLATE DEVICE

TECHNICAL FIELD

The present invention relates to a diagnostic device useful in chemical and particularly biological and biochemical assays. The invention is particularly directed to multiple well filtration devices, such as microtitration plates, able to retain fluids for extended periods of time and, under specified conditions, to remove liquid quickly and completely.

BACKGROUND ART

Diagnostic devices, including test plates, and, in particular, multiple well or microtitration plates, have been used for both quantitative and, especially, qualitative chemical and biological tests for decades. Various designs and configurations have proliferated as the area of enzyme immunoassays has expanded. Test devices and, particularly, plates having a plurality of wells which include microporous membrane filters, have also become routinely used in clinicallaboratories in recent times. This has resulted, at least in part, from development of cell and tissue culture techniques and assays in fields such as virology and immunology.

It is common in the clinical assay to simultaneously run a number of different tests on the same liquid sample, to run duplicate tests, or to perform the same test procedure on a number of different samples. In such instances, it is preferred to employ a multiple well filtration plate, such as a ninety-six well plate. Such test devices have advantages in that they provide a single test apparatus rather than multiple test apparatus and also provide side-by-side comparison of test results within a single device. Such plates, however, have several significant shortcomings. Many of the materials used to form at least the bottom portion of such test devices are porous in nature and permit liquid in the wells to pass through the bottom either by gravity flow or capillary action. Although such liquid loss may be permissible and even desirable in many instances, uncontrolled loss of fluid in many assays leads to inaccurate or unreliable results. This is particularly true in treating or conducting tests on living cells or tissues. In such applications, the biological material is frequently grown or maintained in media of specified composition for periods of from several hours to several days. Losses of even small volumes of liquid can in some instances alter the results drastically.

A second common problem encountered with the use of such multiple well test plates involves a phenomenon known by some as "cross-talk". Such occurrence involves the migration of liquid, sometimes in the form of a pendant drop suspended from the bottom of one well, to an adjacent well. Two causes of the type of migration known as cross-talk are (1) wicking of fluid or diffusion of solutes laterally through the membrane between adjacent wells, and (2) coalescing of pendant drops suspended below the wells. Such migration may lead to spurious results, both when the liquid removed from the wells is to be analyzed or, possibly, when liquid flows back into an adjacent well.

DISCLOSURE OF THE INVENTION

The present invention is directed to a diagnostic test device which includes a plate having at least one well, and preferably a plurality of wells, each well having an open bottom. At the bottom of the well and forming a hydrophobic, liquid-tight seal at the periphery thereof is placed a composite membrane comprising three layers which are, preferably, in intimate contact with one another. Proceeding from the top or upstream side to the bottom or downstream side of the composite membrane, in sequence, the first layer is a reaction or filtration layer formed from a thin, liquophilic microporous membrane, such as a membrane of filtration material. After transfer of a test sample to a well and removal of liquid, in those situations when subsequent reactions are performed on substances retained by the composite membrane, it is the reaction layer which generally forms the site at which reaction occurs. Placed below the reaction layer is a second or sealing layer. This second, preferably porous layer functions as both a means of securing or adhering the reaction layer to a liquophobic barrier layer as well as forming a liquophobic seal at the periphery of the well where the side walls of the well contact the composite membrane. Because of the liquophobic seal, cross-talk by lateral diffusion or wicking is eliminated. Preferred is a hydrophobic material for the second layer. The third or downstream layer is a liquophobic barrier layer. This layer includes a small aperture located substantially at the center of the well. This barrier layer substantially eliminates dripping, enhances isolation of each well in multiple well devices, and inhibits lateral migration of a pendant liquid drop from one well to another well.

In addition to the aforementioned advantages, the multiple well diagnostic plate device of the present invention permits greater or enhanced sensitivity in tests performed with the device as a result of the increased surface area afforded by the porous nature of the reaction layer. In some instances, the substantially increased sensitivity resulting from the substantially higher surface area of the microporous membrane provides results making the difference between operability and inoperability of the particular protocol. Furthermore, the rapid and efficient removal of sample and reagent solutions only after application of a pressure differential permits the solutions to be removed rapidly and completely without the use of a pipette.

BEST MODE FOR CARRYING OUT THE INVENTION

The Diagnostic Plate

Figure 1:
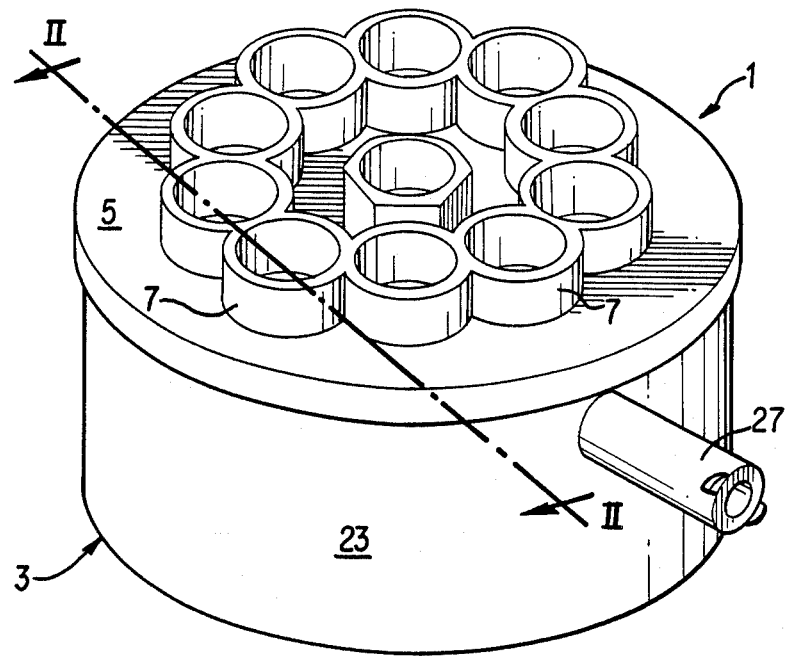
FIG. 1 illustrates a preferred embodiment of the present invention in combination with a manifold.

The diagnostic plate employed in the present application may have a variety of forms and be made from any suitable material. Preferred materials are thermoplastic resins including polyolefins, such as polypropylene, and polystyrene. The plate may contain as few as one well or as many wells as can be arranged within the plate and effectively serviced by the source of differential pressure, i.e., reduced or positive pressure, employed. Filtration plates currently being used typically have ninety-six wells and this number of wells is not incompatible with the present invention. Typically, the wells in such devices are closely spaced for efficiency and economics. As a result, the potential for cross-talk in such devices is enhanced.

The wells themselves may be formed in the shape of cylinders projecting upwardly from a base of the plate or, as preferred, may be formed as cylinders projecting downwardly from an upper surface or plane of the plate. Each of the wells may have vertical or downwardly tapered side walls, the latter forming conical or tapered wells.

The dimensions and shape of each well may be varied depending upon the application of the device. Thus, the well will typically have a cylindrical configuration but other configurations, such as a square or rectangle, may also be used. Likewise, the diameter of the well may vary considerably depending upon such factors as the size of the sample to be used in each well and whether the device is to be used for diagnostic purposes, its most widespread anticipated application, or for separation and isolation of substances.

The size of the liquid sample used and, therefore, the dimensions of the well may also depend on the sensitivity of the reaction performed in the well when the device is used for diagnostic purposes. Typically, the diameter of a well will be from about 1 mm to about 100 mm. Preferably, the diameter of a well will be about 2 mm to about 25 mm. Typically, the height of a well is about 1 to about 75 mm, preferably about 5 to about 10 mm.

The bottom of each well has an opening formed therein. For example, the well may have the configuration of an open cylinder or of a hollow truncated or frustoconical cone. The periphery or brim of the opening to which the composite membrane is adhered generally forms a horizontal surface.

Composite Membrane

Across the bottom of the well and sealed in liquid-tight relationship to the periphery of the well is a composite membrane. The composite membrane comprises at least three layers. The first or uppermost layer constitutes a "reaction layer" which, when the device of the present invention is used for diagnostic purposes, is the layer in or upon which reagents are added and tests are performed. This layer may also be used as a filtration medium to separate liquid and solid components when the material retained by the composite membrane is not intended for further characterization. The material from which this layer is formed, like the other layers, must not react adversely with substances found in either the samples, reagents or solvents employed in the analyses. In addition, the reaction layer must be formed from a liquophilic, microporous membrane, typically having an absolute pore rating of about 0.001 to about 20 microns, preferably about 0.02 to about 8 microns, and most preferaly about 0.2 to about 3 microns. The reaction layer preferably is also skinless. Materials which are suitable for use as the reaction layer also have voids volumes in the range of about 60 to about 90 percent, preferably in the range of about 75 to about 90 percent. Preferred materials are hydrophilic in nature and are, therefore, easily water-wettable and tend to freely pass aqueous solutions. Examples of liquophilic materials which may be used in the present invention include, but are not limited to, polyamides, such as nylon 66, polyvinylidene difluoride, cellulose esters, and nitrocellulose.

Liquophilicity, as used herein, refers to the wettability of the membrane by the liquid(s) with it is contacted. The wettability or liquophilicity of a solid structure, e.g., a membrane, is a function of that structure's critical surface energy and the surface tension of the applied liquid. If the critical surface energy is at least as high as the surface tension of the liquid, the liquid will spontaneously wet the solid structure. For example, a microporous membrane having a critical surface energy of 72 dynes/cm or higher will be wetted by water which has a surface tension of 72 dynes/cm, i.e., it is hydrophilic.

The capability of a porous structure (membrane) to be wetted by a liquid can be determined by placing a drop of liquid on the porous structure. The angle of contact provides a quantitative measure of wetting. A very high angle of contact indicates poor wetting, while a zero angle of contact defines complete or perfect wetting. Materials used in the subject invention as the wettable or liquophilic porous layer are characterized by being readily or spontaneously wetted by the applied liquid and have a low angle of contact with the applied liquid. Indeed, when a drop of a test liquid(s) is placed on a spontaneously wettable or liquophilic microporous membrane layer, the drop of liquid penetrates the layer amd wets the membrane, effectively providing a zero angle of contact therewith.

Suitable materials should also be capable of being treated with and retaining or immobilizing a substance being analyzed and/or a reactant which may be used to perform a specified test or reaction with the substance being analyzed for in a sample. The reactant, which may be of ionic, molecular, or macromolecular nature may be immobilized on the reaction layer by strong physical forces or by being bonded in some manner, such as covalent chemical coupling, to the surface of the microporous, liquophilic reaction membrane layer. As employed herein, the term "surface" or "surface area" refers not only to the gross surface(s) of the structure but also, in those cases where a microporous structure such as a membrane is under consideration, to the surfaces of the micropores, i.e., the interior surfaces of the structure which are contacted by fluid during use. As distinguished from "surface area" or "surface", the exposed planar or gross area of the material is herein referred to as the "reaction layer area", "microporous reaction layer area", "reaction layer membrane area", or the like.

Wettability or liquophilicity is a requisite of the materials used for the microporous reaction layer of the present invention. It is particularly preferred that such materials be capable of being spontaneously wetted. Some of the materials which are suitable or preferred for use as the reaction layer in the present invention are intrinsically hydrophilic or water-wettable. Others may be modified to render them hydrophilic. BIODYNE ® is an N66 polymide, microporous membrane commercially available from Pall Corporation which is inherently water-wettable by virtue of its method of manufacture (see U.S. Pat. No. 4,340,479).

Polyvinylidene fluoride membranes are not inherently water-wettable but can be rendered such by an appropriate surface treatment. Microporous, polyvinylidene fluoride membranes which have been treated to render them hydrophilic are commercially available. As discussed above, wettability or liquophilicity is a function of the critical surface energy of the solid structure and the surface tension of the liquid. Wettability may also be expressed in terms of intrusion pressure which may be defined as the applied pressure required for liquid to penetrate into the pores of the membrane. Although a function of the properties of the liquid used, such as surface tension, materials which are particularly preferred for the reaction layer of the composite membrane have intrusion pressures of or close to zero.

Materials which are preferred for the reaction layer also have large surface areas. This feature permits a greater amount or higher concentration of reactant to be immobilized in the reaction layer. Accordingly, higher sensitivities may be achieved using the test plate of the present invention.

Polyamides preferred for use in the present invention include nylons of the type described in U.S. Pat. No. 4,340,479, which is incorporated herein by reference. As noted above, a membrane material of this description which is particularly useful for the present invention is a microporous, hydrophilic nylon membrane commerically available from Pall Corporation under the trademark BIODYNE ®.

Another preferred membrane useful as the reaction layer is IMMUNODYNETM TM, available from Pall Corporation. IMMUNODYNETM TM is a modified CARBOXYDYNE ® membrane, also available from Pall Corporation. CARBOXYDYNE ® is a hydrophilic, microporous, skinless nylon 66 membrane with controlled surface properties formed by the cocasting process described in U.S. Pat. No. 4,707,266, as discussed below, specifically by cocasting nylon 66 and a polymer containing an abundance of carboxyl groups to form a membrane having controlled surface properties characterized by carboxyl functional groups at its surfaces. IMMUNODYNETM TM membranes may be prepared from CARBOXYDYNE ® membranes by treating them with trichloro-s-triazine in the manner described in U.S. Pat. No. 4,693,985, discussed below.

Also included among the preferred polyamide membranes for the present invention are hydrophilic, microporous, skinless polyamide membranes with controlled surface properties of the type described in (1) U.S. patent application Ser. No. 850,061, filed Apr. 7, 1986, now U.S. Pat. No. 4,707,266, which is a continuation application of U.S. patent application Ser. No. 459,956, filed Jan. 21, 1983, now abandoned, which in turn is a continuation-in-part application of U.S. patent application Ser. No. 346,118, filed Feb. 5, 1982, now abandoned and in (2) U.S. patent application Ser. No. 848,911, filed Apr. 7, 1986, now U.S. Pat. No. 4,702,840, which is a continuation application of U.S. patent application Ser. No. 460,019, filed Jan. 21, 1983, now abandoned which is a continuation-in-part application of U.S. patent application Ser. No. 346,119, filed Feb. 5, 1982, now abandoned.

All of the aforementioned U.S. patent applications are specifically incorporated herein by reference. These hydrophilic, microporous, substantially alcohol-insoluble polyamide membranes with controlled surface properties are formed by cocasting an alcohol-insoluble polyamide resin with a water-soluble, membrane-surface-modifying polymer having functional polar groups. Like the preferred hydrophilic, microporous nylon membranes which do not have controlled surface-modified polar groups present, the polyamide membranes of the present invention having controlled surface properties are also skinless; that is, they are characterized by through pores extending from surface-to-surface which are of substantially uniform size and shape. If desired, however, materials having tapere through pores, i.e., pores which are larger at one surface of the sheet, narrowing as they approach the opposite surface of the sheet, may be used.

The surface-modifying polymers used to prepare the polyamide membranes with controlled surface properties, useful in the present invention, comprise polymers which contain substantial proportions of chemically functional groups, such as hydroxyl, carboxyl, amine, and imine groups. As a result, the membranes include, at their surfaces, high concentrations of functional groups such as hydroxyl, carboxyl, imine, or a combination of any of the above groups which do not react with one another. These polyamide membranes having controlled surface properties have higher concentrations of carboxyl or imine groups at their surfaces than the preferred microporous, hydrophilic, skinless polyamide membranes described above which do not have controlled surface properties, i.e., those which are formed from the preferred polyamide resin but are not cocast with surface-modifying polymer.

The reaction layer may be treated by any method known to one of skill in the art to deposit and/or bind reagents thereto. As indicated above, the reagent may be of an ionic, molecular, or macromolecular nature. When used as a diagnostic tool to provide a visible change, the reagent may be one or a combination of substances which is initially colorless and which, upon reaction with a suitable material, provides an optically measurable response. Other possible variations include the use of suitable labels, such as the formation between the deposited reagent and the material for which testing is being conducted of a complex or compound which is appropriately labeled by any known technique, such as enzymatic/substrate labels or the like.

Although treatment of the reaction layer with a suitable reagent(s) may be performed at the time at which diagnostic tests are to be performed, including addition of the test reagent(s) both immediately preceding and following introduction of the sample containing the analyte to the well(s), the present invention is expected to have greatest applicaion to, and a preferred embodiment includes, a composite membrane in which the reaction layer has been pretreated with at least one test reagent. Typically, pretreatment is conducted after the composite membrane has been sealed to the wells but before the device is shipped to a user. If the reagent(s) is not heat sensitive, the membrane may be treated before assembling the composite membrane.

A useful method of binding reagents of a molecular nature, especially macromolecules, and particularly those of a biological nature, is disclosed in U.S. Pat. No. 4,693,985, specifically incorporated herein by reference. This patent describes a method for immobilizing a wide range of biologically active substances as acceptor molecules on active membranes. The acceptor-bound membranes described in the application are capable of immobilizing and binding a wide variety of biologically-active compounds, specifically ligands, to the acceptor molecules. Using such reaction layers or membranes permits the testing of bodily fluids, such as blood, serum, plasma, urine, saliva, and the like, and testing for particular substances by chemical assays or immunoassays, such as those where a specific label is employed, such as one indicating enzyme activity or an electromagnetic energy absorbing and/or emitting label, such as a fluoroescent label. The macromolecules used as reagents and bound to the reaction layer or which are assayed for using the device of the present invention generally include materials of a biological nature and are frequently proteinaceous in nature. The reagent or acceptor molecule bound directly to the reaction layer or the ligand being tested for include such substances as immunoglobulins or antibodies, either polyclonal or monoclonal, antigenic substances, apoproteins, receptors, glycoproteins, lectins, carbohydrates, hormones, enzymes, carrier proteins, heparin, coagulation factors, enzyme substrates, inhibitors, cofactors, nucleic acids, etcetera.

Placed below, preferably in intimate contact with or, most preferably, adhered, bonded, or otherwise secured to the reaction layer, particularly at the periphery of each well, is a porous sealing layer which serves several purposes. Strongly preferred for use as a sealing layer is a very porous liquophobic structure. The term "liquophobic" as used herein is effectively the obverse of the term "liquophilic", that is, a liquophobic material has a critical surface energy lower than the surface tension of the applied liquid and is not readily or spontaneously wetted by the applied liquid(s). Liquophobic materials are characterized, then, by a high contact angle between a drop of liquid placed on the surface and the surface. Such a high contact angle indicates poor wetting. The porous sealing layer assists in bonding the reaction layer to the barrier layer. It also makes it possible to form a liquophobic seal at the periphery of the well, thereby eliminating cross-talk by diffusion or wicking. The use of such material in the sealing layer also provides the composite membrane with the ability to withstand or maintain a pressure differential. For example, it prevents, without the application of vacuum or high pressures, penetration of liquid through the composite membrane and the concomitant loss of liquid from the well by dripping. Thus, at specified pressure conditions, generally close to or at atmospheric pressure, liquid is retained within a well. However, when reduced pressure is applied to the downstream side of the composite membrane or super atmospheric pressure is applied to the upstream side of the membrane, liquid readily drains from the well.

Materials suitable for use as the sealing layer, in addition to being liquophobic, preferably are hydrophobic and are also significantly more porous than the reaction layer. Such material may be present in sheet or fiber form, either woven or unwoven. Suitable materials include polyamides, linear polyesters, such as esters of ethylene glycol and terephthalic acid, polyolefins, such as polypropylene, polyethylene, polymethylpentene, and polyisobutylene, as well as copolymers formed by copolymerizing the monomers used to form the aforementioned homopolymers, such as ethylene-propylene copolymers. Mixtures or blends of such polymers can also be used. The polyolefins are preferred and polypropylene is particularly preferred.

The third or downstream layer constitutes a barrier layer which, preferably, is in intimate contact with or, most preferably, is adhered, bonded, or otherwise secured to the sealing layer, particularly at the periphery of each well. It is this layer, provided with at least one, and preferably only one, aperture located substantially at the center of the well, which permits a drop of liquid to pass from the well, under application of positive or negative gauge pressure, i.e., super atmospheric pressure applied upstream of the composite membrane or reduced pressure applied downstream of the membrane, and to drop from the plate without radial migration to another well. The apertures can also serve as restriction means, controlling the flow rate of liquid through the composite membrane. Thus, the barrier layer, because of the nature of the material used therein, i.e., a highly liquophobic, preferably hydrophobic, material, enhances isolation between wells and forces the liquid passing through the composite membrane to form small drops at the hole in the barrier layer. These drops, rather than spreading radially when passing through a porous or microporous liquophilic material (such as the material of the reaction layer used alone or in conjunction with the sealing layer) and forming a small contact angle with the surface of such material, tend, when passing through the barrier layer, to form a large contact angle with the surface of liquophobic material. Thus, even if the device is raised at one end so that the bottom surface is not completely horizontal, liquid drops passing through each well tend to drop from the device rather than rolling to one side and potentially contaminating fluid in an adjacent well.

The size and shape of the apertures formed in the barrier layer depend on a number of variables including the porosity of the barrier layer, the number of apertures in the barrier layer, the porosity and number of apertures formed in the other layers (discussed below), the number of wells, the flow rate sought, ease of manufacturing, etc. However, when a single aperture is used in the barrier layer of each well, it may be formed in a variety of shapes. A suitable size for the aperture is about 1/32 to about ¼ inch. An aperture or hole simply formed in the shape of an "X" in the barrier layer, i.e., without a corresponding aperture in the sealing layer or reaction layer, provides an operable system.

The material used to form the barrier layer should have a greater liquophobicity than either the reaction layer or the sealing layer and may be either microporous or nonporous. Another way of expressing the suitability of a material as the barrier layer relates to the wetting resistance characteristics of the material. A suitable material should be capable of resisting a liquid intrusion pressure greater than to the height of the column of liquid above the barrier layer, i.e., the height of the liquid placed in the well. Suitable materials include polyolefins, such as polypropylene, polyhalogenated polyolefins, particularly perfluorinated polyolefins, such as polytetrafluoroethylene, and polyvinylidene difluoride, as well as sulfones. Polytetrafluoroethylene is most preferred.

In addition to the aperture formed in the liquophobic barrier layer, the reaction layer may also be provided with at least one, and preferably no more than one, aperture. When a single aperture is provided in the reaction layer, the diameter of the aperture may be in the range of about 3 to about 100 microns. When present as a plurality of apertures, each aperture may have a diameter of about 3 to about 100 microns. The choice of using a membrane either with or without an aperture in the reaction layer is determined by such factors as the source and type of vacuum or pressure apparatus employed to force a liquid through the composite membrane, the number of wells present in the device, the overall porosity of the composite membrane, the porosity or bubble point characteristics of the reaction layer, and the dimensions of the aperture(s) in the barrier layer. All of these factors affect the rate of fluid flow through the membrane at a given pressure drop.

The provision of one or more apertures in the reaction layer of the composite membrane in each well assures total voiding of liquid through the composite membrane when positive or negative gauge pressures are employed. When the reaction layer is provided with an aperture, a continuous, rather than an intermittent, application of positive or reduced pressure is necessary since the vacuum or positive pressure will be continuously bleeding away. However, depending on the factors listed above, when a reaction layer having no apertures passing therethrough is provided in the composite membrane, a continuous application of positive or reduced pressure, preferably the latter or a single or intermittent application of positive or negative gauge pressures using, for instance, a syringe and check valve combination may be employed. These latter alternatives are generally preferred.

In some instances when manufacturing the composite membrane of the present invention, it is desirable to initially provide each of the layers with the appropriate number of apertures. Thus, a needle(s) may be used to simultaneously form the apertures in each layer in alignment with each other. However, with the porous sealing layer, the aperture will usually not be much larger than the existing pores and when a fibrous material is used, the fibers will generally move back to the position they occupied before insertion of the needle. In this embodiment, the diameters of the apertures in the reaction and barrier layers are the same. This embodiment provides for ease of manufacturing in that the apertures may be formed after the composite membrane is assembled and the layers are secured to one another.

Typically, reduced pressure or vacuum-assisted fluid flow is accomplished with the present invention by means of a vacuum manifold which is provided with a means for connection to a vacuum source, such as a projecting tube which can be inserted into vacuum tubing. Such manifolds also include a means to form an air-tight seal between the well(s)-containing diagnostic plate device and the manifold, such as a pliable gasket or the like. Such manifolds commonly include a vertical wall portion, the internal surface of which configurationally conforms to the outer surface of a vertical wall portion of the plate device such that mating of the two wall surfaces occurs. Other designs, however, may be employed, such as the diagnostic plate device being provided with an internal wall surface which mates with an external wall surface of the manifold. Alternative structures in which mating surfaces of the manifold and diagnostic plate device are provided and in which an air-tight seal may be established may also be employed with the present invention.

In use, a first test or reagent liquid is normally placed in each of the wells of the diagnostic plate device, and the device is then inserted into the vacuum manifold such that the gasket or sealing means contacts mating surfaces in both the diagnostic plate device and the manifold. Communication between a source of vacuum and the manifold is then established. As the pressure in the manifold decreases, the diagnostic plate device is drawn against the gasket, improving the seal. As this occurs, liquid is drawn through the wells into the vacuum line and to a waste trap. Solutions of samples to be tested or reagents are then introduced into each of the wells.

To provide a means for isolating and retaining fluids passing through the diagnostic plate device of the present invention for those situations in which it is desirable to conduct further tests on the liquid, a second modified form of the diagnostic plate device may be used within the vacuum manifold. The modified form of the plate is positioned intermediate the vacuum manifold and the diagnostic plate device in which test samples are analyzed. The modified form of the device is one in which the wells have solid impermeable bottoms, that is, the wells do not have open bottoms covered with the composite membrane of the present invention but rather the membrane is replaced with the same material from which the walls of the wells are made or some similar material. In most cases, the modified plate is of unitary construction in which the side walls and bottom are formed integrally in a single step. The sealing means is still maintained between the diagnostic plate device of the present invention and the vacuum manifold when the device is placed into operation.

In some situations, it may be desirable to use the diagnostic plate device of the present invention in situations where a vacuum line connected to a centralized source of vacuum or a vacuum pump is not available. An embodiment of the present invention, nevertheless, permits analysis in such instances. The manifold employed includes a modified outlet means for connecting to a vacuum source. Specifically, the outlet includes a one-way valve of a type generally known to the valve art which permits fluids to be withdrawn from the manifold but does not permit fluids to enter the manifold. In addition, the connection means permits a syringe tip to be inserted into the manifold so that a large syringe may be used as the vacuum source. Such a means for connection to a syringe tip may be a Luer locking device or the like. When a syringe is used as the vacuum source, this will normally be able to displace a much smaller volume of air than will a continuously operating vacuum pump. Accordingly, the vacuum manifold and diagnostic plate device adapted to be used with the manifold will be of a smaller size with fewer than 96 wells which is a typical number for such multiple well diagnostic plate devices.

As with the larger diagnostic plate device described above, the periphery of the plate may have any suitable configuration as long as adequate mating and sealing surfaces are provided between the manifold and the diagnostic plate device. To sufficiently reduce the volume of the manifold when the device is to be used with a syringe as the source of vacuum, the periphery of the plate is preferred to have a circular configuration, such as that shown in FIG. 1, the wells also preferably being arranged in a circular configuration. With such a configuration, various means may be provided for the attachment of the plate to the manifold including that described above in which the well-containing plate is merely pressed into the manifold with a sealing means separating two mating surfaces. Alternatively, in addition to sealing means, threading or bayonet mounts may be provided on corresponding mating surfaces of the plate and manifold. However, a preferred structure is one that is disposable in which the diagnostic plate is formed integrally with the manifold. Preferably, the integrally formed structure also includes a means for trapping liquids in the manifold. With this structure, possibly contaminated fluids are trapped within the device, and the entire article, including trapped liquids, could be disposed of while minimizing risks associated with contamination.

Figure 2:
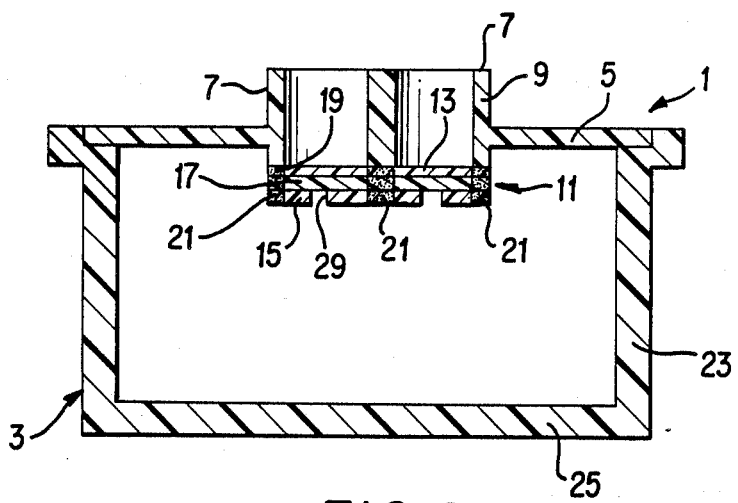
FIG. 2 is a sectional view of FIG. 1 taken along line II—II.
Figure 3:
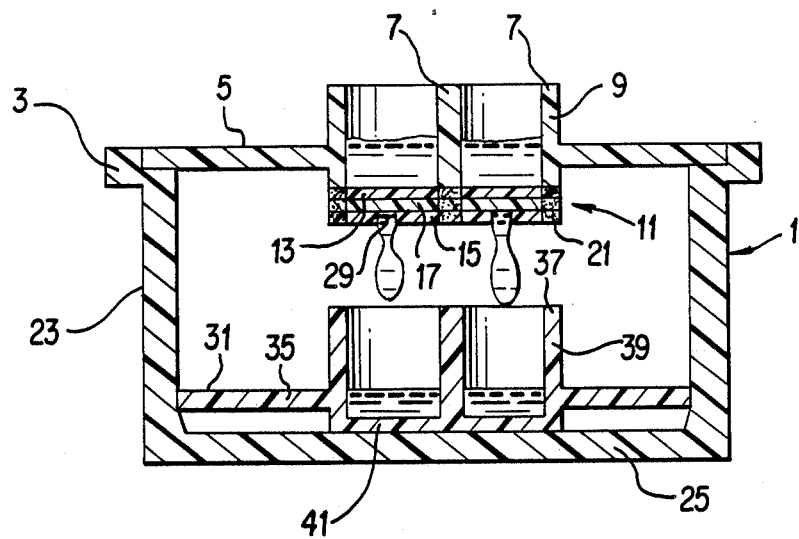
FIG. 3 is a sectional view of an embodiment of the present invention which includes an upper well-containing plate portion having a composite membrane at the bottom opening of each well and a lower receptacle portion.

FIGS. 1 to 3 illustrate preferred embodiments of the present invention. As shown in the FIGS. 1 and 2, the device is formed from a multi-well diagnostic plate or plate portion 1 and a vacuum manifold or manifold portion 3. In one of the preferred embodiments of the present invention, the elements 1 and 3 are formed as a separate multiple well diagnostic plate and vacuum manifold, one placed in the other and having a sealing surface formed therebetween, as described above. Most preferred, however, is a structure in which the device is formed integrally. In this latter embodiment, no sealing means is necessary since what constitutes the multiple well diagnostic plate portion 1 is not detachable from the manifold portion 3. This embodiment is intended to be disposable. Other than this feature and the vacuum connecting means, the embodiments are substantially similar in most respects. Thus, the diagnostic plate portion 1 is provided with an upper or top wall 5 having located therein one or more wells 7. The wells are defined by a wall portion 9 which is preferably vertical or substantially vertical, although the wall portion may have a downward taper. The well is provided with openings at both the top and bottom ends. Sealed to the bottom end 19 of the well is composite membrane 11 formed from an upper reaction layer 13, a bottom barrier layer 15 having an aperture 29 passing therethrough, and a sealing layer 17 located intermediate the reaction layer 13 and the barrier layer 15. As a result of the heat process used, a dense, somewhat compacted, liquophobic zone 21 is provided at the periphery of each well which prevents lateral flow or "cross-talk" of fluids, particularly liquids, between wells.

The manifold portion 3 comprises a side wall or walls 23 and bottom wall 25. The upper plate or wall 5, side wall 23, and bottom wall 25 define a housing in which the wells are located. A vacuum connection means 27 is provided to communicate the housing or manifold portion with a source of vacuum (not shown).

One preferred purpose of the sealing layer 17 is to seal the barrier layer 15 to the reaction layer 13. Another function served by the sealing layer is to provide a liquophobic seal at the periphery or rim of each well where the composite membrane is secured to the periphery of the opening at the bottom of the well. Such a seal is typically accomplished by means of a heat, and preferably combined with pressure, treatment. Heat-sealing methods using radiant heat or ultrasonic sealing techniques with apparatus, such as heater blocks or welding horns, respectively, may be employed. It is the liquophobic seal formed at the periphery of the opening of each well by such treatment which prevents liquid passing through the composite membrane from diffusing or migrating radially and possibly contaminating another well.

The embodiment of the present invention illustrated in FIG. 3 permits liquid which has passed through a well of a diagnostic plate according to the present invention, such as that described above, to be isolated from a test sample and retained. In this embodiment, the reference numerals common to FIG. 3, and FIGS. 1 and 2, describe substantially the same elements. The major distinction to be drawn between the embodiment of the present invention illustrated in FIGS. 1 and 2 and that of FIG. 3 is the inclusion within the manifold portion 3 of a second or receiving plate 31 having a plate portion 35 with one or more wells 37 located therein, each well defined by a wall portion 39. The dimensions and configurations of the plate portion 31, wall 35, wells 37, and wall portion 39 are preferably the same or similar to those of the corresponding top wall 5, wells 7, and wall portions 9 of the diagnostic plate portion 1. The major difference between the upper diagnostic plate portion 1 and the second plate or receptacle 31 is that the latter substitutes a solid impermeable bottom 41 for the composite membrane 11 of the former. The receptacle plate 31 is arranged within the manifold 3 in such a manner that the second plate (and particularly the well(s) 37 located therein) is aligned with and in liquid receiving relationship to the first plate (and particularly the wells 7 located in the diagnostic plate 1). This permits liquid passing through each one of the wells 7 in the diagnostic plate to be isolated from an adjacent well and, after passing through the composite membrane 11, to be retained in a solid bottom well 41 of the second plate 31 corresponding to the well in the upper plate through which it just passed.

The composite membrane of the present invention may be assembled by a variety of techniques. Thus, each of the separate layers may be overlaid and the separate layers sealed to one another and to the bottom of each well in a single heat-sealing procedure. This may be accomplished by superposing the individual layers, i.e., the reaction layer, the sealing layer, and the barrier layer, over the open bottom ends of the wells such that the apertures in the barrier layer and, where appropriate, other layers are located substantially at the centers of each well. Heat is then applied from the barrier layer side of the membrane to secure the separate layers to one another and also to form a hydrophobic seal between the composite membrane and the bottom edge surface of the wall of each well. Heat is applied either directly in the form of radiant heat by a heater block or as ultrasonic energy using a welding horn. In this manner, the reaction layer is sealed to the edges of each of the wells and, simultaneously, the sealing layer fuses the reaction layer to the barrier layer.

To facilitate handling of the layers of material forming the composite membrane, rather than superpose each layer individually over the bottoms of the wells, it is preferred that the edges of the sheets of material forming the layers may be welded or tacked to one another to provide a preliminary composite membrane. The sealing of the composite structure to the bottom edge surfaces of the wells and possibly of the layers to each other occurring, as indicated above, when heat is applied to the layers of material superposed on the plate.

Alternatively, although less preferred, rather than adhering the edges of the separate sheets such as by tacking or the like, the three layers may be secured to one another to form the composite membrane in a first step and the formation of a liquid-tight seal to the bottom of the wells may be achieved in a second step. Other alternatives include bonding the sealing layer to the reaction layer in a first step, such as that described in U.S. patent application Ser. No. 107,918, filed Oct. 13, 1987, which in turn is a continuation of U.S. patent application Ser. No. 685,042, filed Dec. 21, 1984, and incorporated herein by reference. According to this method, microfibers are directed in a stream toward a sheet of the reaction layer, generally after the fibers are extruded from a fiberizing die and attenuated in one or more gas streams. The microfibers are extruded at an elevated temperature and after contacting the microporous reaction layer are cooled to form a composite, two layer membrane containing a web of microfibers as a sealing layer secured to the reaction layer. A similar procedure may be employed in which the sealing layer is formed as a sheet and, while at an elevated temperature, is placed in contact with a sheet of the microporous reaction layer. The hydrophobic barrier layer is then applied to the two layer composite membrane by a heat bonding procedure.

In use, a solution containing the sample to be analyzed and one or more reagent solutions may be added simultaneously or, in most instances, preferably, sequentially to each well of the multiple well diagnostic plate. Under appropriate temperature conditions, the solutions are added to and removed from each well, in timed sequence to allow sufficient time for reactions to take place in solution or on the surface of the reaction layer before the addition or removal, as appropriate, of a solution. In many instances, molecular species, particularly macromolecular species, such as nucleic acids, antibodies, antigens, or enzyme-labelled conjugates are adsorbed. Weakly or non-adsorbed molecules are removed from the surface of the composite membrane by washing between steps with suitable buffers. When the reaction sequence is completed, a labelled product, such as a visible colored or fluorescent product, remains or is formed on the surface of the membrane within the well.

To perform quantitative assays, the well(s)-containing plates are placed in a suitable reading device, typically containing a source and a detector of radiation. The colored or light emitting product may then be quantitatively measured using either transmitted or reflected light.

Solutions may be introduced to the well using a pipette. However, after a suitable period for reaction to occur, the solutions may be removed by application of vacuum or elevated pressure. Furthermore, in some instances, it may be unnecessary to remove one solution completely before the addition of another solution. Rather, one solution may be added as the previous solution is being removed or, in some instances, a second solution may be added while the first is still present and the two solutions allowed to mix before removal.

We claim:

1. A diagnostic test device comprising:
   a plate,
   at least one well formed in said plate, said at least one well having an open bottom, and
   a composite membrane having at least three layers including, sequentially, a microporous liquophilic reaction layer, a sealing layer, and a liquophobic barrier layer having at least one aperture therein for each said well and located substantially at the center of the well, said composite membrane coextensive with the bottom of said at least one well and forming a liquophobic, liquid-tight seal at the periphery of the well.

2. The diagnostic test device of claim 1 wherein said reaction layer comprises a hydrophilic material.

3. The diagnostic test device of claim 1 wherein said sealing layer comprises a synthetic, thermoplastic web of microfibers.

4. The diagnostic test device of claim 1 wherein said liquophobic, liquid-tight seal is a hydrophobic liquid-tight seal.

5. The diagnostic test device of claim 1 wherein said reaction layer includes a hole located at substantially the center of said well.

6. The diagnostic test device of claim 1 wherein said microporous reaction layer comprises a biologically inert polymeric material.

7. The diagnostic test device of claim 1 wherein said microporous reaction layer is formed from a polyamide or polyvinylidene difluoride.

8. The diagnostic test device of claim 1 further including a test reagent immobilized on said reaction layer.

9. The diagnostic test device of claim 1 wherein said barrier layer is formed from a material having a greater liquophobicity than that of either the reaction layer or the sealing layer.

10. The diagnostic test device of claim 1 wherein said at least one aperture consists of one aperture.

11. The diagnostic test device of claim 1 wherein said three layers are in intimate contact with one another.

12. The diagnostic test device of claim 11 wherein said three layers are bonded to one another.

13. The diagnostic test device of claim 1 wherein said at least one well comprises a plurality of wells.

14. The diagnostic test device of claim 13 wherein said composite membrane covers and is substantially coextensive with the bottoms of all of said wells.

15. The diagnostic test device of claim 1 wherein said device is adapted to be operatively associated with a differential pressure.

16. The diagnostic test device of claim 15 wherein said differential pressure is a reduced pressure.

17. The diagnostic test device of claim 1 wherein said microporous reaction layer comprises a hydrophilic, surface-modified polyamide.

18. The diagnostic test device of claim 17 wherein said surface-modified polyamide is a surface-modified nylon 66.

19. The diagnostic test device of claim 1 wherein said sealing layer comprises a hydrophobic material.

20. The diagnostic test device of claim 19 wherein said hydrophibic sealing layer is formed from a polyamide, a linear polyester, a polyolefin, a copolymer of two or more olefins, or mixtures of the aforementioned polymers.

21. The diagnostic test device of claim 20 wherein said hydrophobic sealing layer comprises polypropylene.

22. A diagnostic test system comprising:
   (1) a diagnostic test device including:
      (a) a plate,
      (b) at least one well formed in said plate, said at least one well having an open bottom, and
      (c) a composite membrane having at least three layers including, sequentially, a microporous liquophilic reaction layer, a sealing layer, and a liquophobic barrier layer having at least one aperture therein for each said well and located substantially at the center of the well, said composite membrane coextensive with the bottom of said at least one well and forming a hydrophobic, liquid-tight seal at the periphery of the well; and
   (2) means for generating a differential pressure operatively associated with said diagnostic test device.

23. The diagnostic test system of claim 22 wherein said at least one aperture consists of one aperture.

24. The diagnostic test system of claim 22 wherein said differential pressure generating means comprises a vacuum manifold adapted to be operatively associated with a means for generating a reduced pressure.

25. The diagnostic test system of claim 24 wherein said vacuum manifold is in air-tight sealing relationship with said diagnostic test device.

26. The diagnostic test system of claim 24 wherein said vacuum manifold is formed integral with said diagnostic test device.

27. A diagnostic test device comprising:

(a) a first plate,
  at least one well formed in said first plate, said at least one well having an open bottom, and
  a composite membrane having at least three layers including, sequentially, a microporous, liquophilic membrane reaction layer, a sealing layer, and a liquophobic barrier layer having at least one aperture therein for each said well and located substantially at the center of the well, said composite membrane coextensive with the bottom of said at least one well of said first plate and forming a liquophobic liquid-tight seal at the periphery of the well; and
(b) a second plate in liquid receiving relationship with said first plate,
  at least one well having an impermeable bottom in said second plate to receive liquid from said at least one well in said first plate.

28. The diagnostic test device of claim 27 wherein said at least one aperture consists of one aperture.

29. A diagnostic test system comprising:
(1) a diagnostic test device including:
  (a) a first plate,
  (b) at least one well formed in said first plate, said at least one well having an open bottom, and
  (c) a composite membrane having at least three layers including, sequentially, a microporous, liquophilic membrane reaction layer, a sealing layer, and a liquophobic barrier layer having at least one aperture therein for each said well and located substantially at the center of the well, said composite membrane coextensive with the bottom of said at least one well of said first plate and forming a liquophobic liquid-tight seal at the periphery of the well;
(2) means for generating a differential pressure operatively associated with said diagnostic test device; and
(3) a second plate located intermediate and in operative relationship with said diagnostic test device and said differential pressure generating means, said second plate in liquid receiving relationship with said first plate,
  at least one well having an impermeable bottom located in said second plate to receive liquid from said at least one well in said first plate.

30. The diagnostic test system of claim 29 wherein said at least one aperture consists of one aperture.

31. The diagnostic test system of claim 29 wherein said differential pressure generating means comprises a vacuum manifold adapted to be operatively associated with a means for generating a reduced pressure.

32. The diagnostic test system of claim 31 wherein said vacuum manifold is in air-tight sealing relationship with said diagnostic test device.

33. The diagnostic test system of claim 31 wherein said second plate is located within said vacuum manifold.

34. The diagnostic test system of claim 31 wherein said vacuum manifold is formed integral with said diagnostic test device.

35. The diagnostic test system of claim 34 wherein said second plate is located within said vacuum manifold.

* * * * *